(12) United States Patent
Brockett et al.

(10) Patent No.: US 12,172,024 B1
(45) Date of Patent: Dec. 24, 2024

(54) METHOD FOR ELECTROMAGNETIC ABSORPTION IN BIOLOGICAL TISSUES

(71) Applicant: EVANESC THERAPEUTICS, INC., Canoga Park, CA (US)

(72) Inventors: Timothy J. Brockett, Malibu, CA (US); Mehran Matloubian, Encino, CA (US); Gregg A. Hollingsworth, Tempe, AZ (US)

(73) Assignee: EVANESC THERAPEUTICS, INC., Encino, CA (US)

( * ) Notice: Subject to any disclaimer, the term of this patent is extended or adjusted under 35 U.S.C. 154(b) by 1073 days.

(21) Appl. No.: 17/080,699

(22) Filed: Oct. 26, 2020

(51) Int. Cl.
*A61N 1/40* (2006.01)
*A61B 18/18* (2006.01)
*A61N 1/06* (2006.01)
*A61N 2/02* (2006.01)
*A61B 18/00* (2006.01)

(52) U.S. Cl.
CPC ............... *A61N 1/40* (2013.01); *A61B 18/18* (2013.01); *A61N 1/06* (2013.01); *A61N 2/02* (2013.01); *A61B 2018/00702* (2013.01)

(58) Field of Classification Search
CPC . A61N 1/06; A61N 1/40; A61N 2/002; A61N 2/004; A61N 2/006; A61N 2/008; A61N 2/02; A61B 18/18; A61B 18/1815
See application file for complete search history.

(56) References Cited

U.S. PATENT DOCUMENTS

| | | | |
|---|---|---|---|
| 5,082,517 A | 1/1992 | Moslehi | |
| 6,131,577 A * | 10/2000 | Nicholson | A61B 18/00 607/101 |
| 7,348,182 B2 | 3/2008 | Martin et al. | |
| 7,805,201 B2 | 9/2010 | Palti | |
| 8,364,237 B2 | 1/2013 | Stone et al. | |
| 9,993,294 B2 | 6/2018 | Turner et al. | |
| 10,213,246 B2 | 2/2019 | Toth et al. | |
| 10,252,073 B2 | 4/2019 | Alphandery et al. | |
| 10,624,696 B2 | 4/2020 | Deem et al. | |
| 10,772,162 B2 | 9/2020 | Parsche | |
| 2002/0026188 A1* | 2/2002 | Balbierz | A61B 18/1206 606/41 |
| 2019/0336211 A1 | 11/2019 | Pare et al. | |
| 2020/0319275 A1 | 10/2020 | Chen et al. | |

FOREIGN PATENT DOCUMENTS

| | | | | |
|---|---|---|---|---|
| WO | WO2019133606 | * | 7/2019 | ......... A61B 18/1206 |
| WO | WO-2019133606 A1 | * | 7/2019 | ......... A61B 18/1206 |

* cited by examiner

*Primary Examiner* — Carrie R Dorna
(74) *Attorney, Agent, or Firm* — Richard T. Ogawa; Ogawa P.C.

(57) ABSTRACT

In biological tissues, exposure to electromagnetic fields usually induces actuation and vibration of the underlying molecules which, from the perspective of the electromagnetic device, manifests as power absorption. It has been shown that increased power absorption of a low-power RF source can have positive enhancement in therapeutic, medical, and scientific procedures. However, often the enhanced power absorption is limited due to the electromagnetic properties of the tissue being treated. This invention introduces a method to modify the native electromagnetic properties of a targeted biological tissue to increase and enhance the electromagnetic power absorption within and increase treatment efficacy.

20 Claims, 5 Drawing Sheets

METHOD FOR ELECTROMAGNETIC ABSORPTION IN BIOLOGICAL TISSUES

CROSS-REFERENCES TO RELATED APPLICATIONS

Not Applicable

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Electromagnetic fields have shown to cause biological response in many types of tissues and its application is common in many therapeutic, medical, and scientific procedures. In biological tissues, exposure to electromagnetic fields usually induces actuation and vibration of the underlying molecules which, from the perspective of the electromagnetic device, manifests as power absorption. The amount of power absorbed depends on both the strength of the electromagnetic field and the electromagnetic properties of the tissue.

It has been shown that increased power absorption can have positive enhancement in therapeutic, medical, and scientific procedures. For example, in capacitively coupled treatment of tumors using low-power RF (U.S. Pat. No. 7,805,201), improvement in the efficacy of treatment is directly correlated with increase in power density (and subsequent power absorption) in the tumor. The higher power absorption enhances the interference with the dividing cancer cells during mitosis, causing increased apoptosis and growth inhibition within the tumor cells. Since the interference only occurs in dividing cells, healthy, non-dividing cells are not impacted. As such, increasing the amount of targeted power absorption in biological tissues would be highly beneficial.

Non-invasively increasing the power absorption in a desired tissue such as a tumor is usually accomplished by increasing the strength of the electromagnetic fields within the targeted volume that contains the tissue. This can be accomplished by increasing the electric or magnetic field strength by increasing the applied voltage or current, respectively, of the electromagnetic device which increases the incident power of the electromagnetic fields. In many cases, however, limitations in the amount of available power and the maximum voltage and/or current of the source, prevent further increase in the power delivered and hence absorbed by the desired tissue. In addition, this approach does not discriminate between various tissues within the targeted volume. Consequently, in applications where there are a variety of tissues in close vicinity of each other (as in the human/animal body), power is likely absorbed in tissues where it is not desired or needed, leading to wasted power and limiting the amount of power absorbed by the desired tissue. In addition, the higher electromagnetic fields can lead to excessive heating of the skin causing discomfort for the patient.

With limitations of the electromagnetic source, the only way to further increase power absorption is to modify the electromagnetic properties of the targeted material. In biological tissues, dielectric and magnetic loss is governed by a frequency-dependent Debye relationship. In general, this Debye curve shows a flat response except for one or more regions of frequency bandwidth where a peak in electromagnetic loss is observed. This electromagnetic loss can be dielectric or magnetic in nature where electromagnetic energy is absorbed and dissipated as heat generated by mechanical movement of molecules and atoms. For most materials, including biological tissues, this peak happens at relatively lower frequencies of the electromagnetic band, usually below 1 MHz.

A unique limitation often occurs when one applies incident electromagnetic energy in treatment of cancerous tumors. It has been demonstrated that the division of tumor cells are disrupted at frequencies somewhere between 50 kHz to 500 kHz. A conundrum appears when the frequency where the dividing cells are most disrupted is not necessarily the same frequency where dielectric or magnetic loss is maximized or significant. As such, the ability to maximize the efficacy of the treatment by increasing power absorption is severely limited, especially when the electromagnetic source is also power limited. Methods to solve this conundrum clearly benefit the treatment options in these cases.

BRIEF SUMMARY OF THE INVENTION

In this invention, we introduce a method to modify the electromagnetic properties of the targeted tumor using various solutions and suspensions that will maximize dielectric and/or magnetic loss at a particular frequency of incident electromagnetic energy.

The method will involve first determining the frequency band where maximized dielectric or magnetic loss is located for the type of tissue or material (cancer cell, cell culture medium, human/animal tissue, etc.) that will be targeted by the electromagnetic energy. Secondly, a liquid, semi-liquid, or gel solution/suspension with tailored electromagnetic properties will be fashioned and injected or incorporated within the targeted tissue or material with the intention to change the frequency band of maximized dielectric or magnetic loss to match that of the frequency of the incident electromagnetic energy.

Determination of the proper solution/suspension must be done externally and will require a sample of the targeted tissue/material of interest. After determining the native electromagnetic properties of the tissue (by using one of several well-established techniques), a companion solution/suspension will be tailored to shift the frequency band of maximized dielectric or magnetic loss to the desired operating frequency. Finding the correct solution/suspension that can accomplish this will require specific concentrations of additives, such as saline, sugar, or other molecules that can shift the peak loss to the desired frequency band.

The targeted tissue will be modified by either injecting the solution/suspension directly into the tumor or incorporation by other methods such as simple mixing, by surgery, intravenously, etc. Once incorporated, treatment can be conducted by using an electromagnetic apparatus such as an antenna or wave-launcher, or other electronic application techniques such as capacitive or inductive coupling and direct connection, to apply incident electromagnetic energy to the now modified targeted tumor/tissue/material.

Medical or biological applications that this apparatus can be used for can include, but not limited to, non-invasive solid tumor cancer treatment, general cancer treatment, electric field therapy for depression, stimulation of tissues, or other low-power treatments using electromagnetic energy.

DETAILED DESCRIPTION OF THE INVENTION

Figure 1:
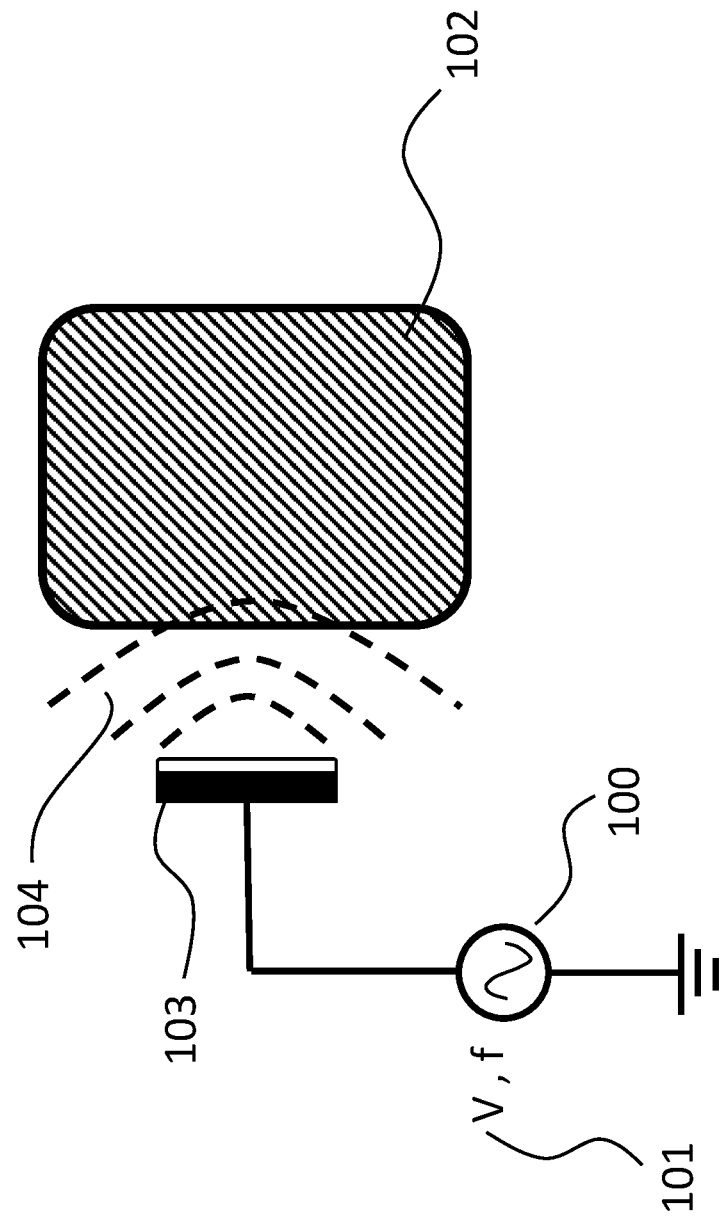
FIG. 1 is a diagram of electromagnetic wave/field at a particular frequency incident upon a target material or biological tissue.

The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of embodiments. Thus, the present invention is not intended to be limited to the embodiments presented but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details.

Please note, if used, the labels left, right, front, back, top, bottom, forward, reverse, clockwise and counterclockwise have been used for convenience purposes only and are not intended to imply any particular fixed direction. Instead, they are used to reflect relative locations and/or directions between various portions of an object. Additionally, the terms "first" and "second" or other like descriptors do not necessarily imply an order but should be interpreted using ordinary meaning.

The invention describe here is a method to increase the power absorption in biological tissue when illuminated with an electromagnetic wave at a particular frequency. This will be accomplished by incorporating a tailored-designed liquid solution or suspension into a targeted tissue, liquid, or region with the aim to change the electromagnetic properties of the targeted tissue or region and increasing the dielectric or magnetic loss.

A specific application of this method involves the treatment of solid tumor cancers such as breast cancer or pancreatic cancer using low-power radio frequency. Based on one postulated mechanism of action, electric fields interfere with the dividing cancer cells during mitosis causing the cancer cells to undergo apoptosis or arrest division, causing the tumor to stop growing or shrink. The electric fields do not impact non-dividing cells so there is no harmful impact to the non-dividing healthy cells. Effectiveness of the electric fields in disrupting the division of the cancer cells depends on several factors including the frequency of the RF source, the magnitude of the electric fields, and on the relative orientation (or polarization) of the electric fields and the axis of the dividing cells.

Different types of cancer cells respond to different frequencies of an electromagnetic field source. For example, it has been demonstrated that for several types of glioblastoma cancer cells, an operating frequency of around 200 KHz is the optimum frequency to kill the cells while for lung cancer cells the optimum frequency has been demonstrated to be around 150 KHz. In addition, it has been shown, that the efficacy of this type of treatment improves with an increase in electromagnetic power density within the targeted tumor and substantially enhanced when increased electromagnetic power densities beyond a minimum is present.

At a fixed frequency of the electromagnetic wave/field, the electromagnetic properties, including the dielectric permittivity, magnetic permeability, and the dielectric and magnetic loss of an unmodified, native biological tissue is fixed. In other words, at a fixed frequency, the power density (or the amount of power dissipated within a volume) within the targeted tissue depends only on the strength of the electromagnetic field present within the tissue. In particular, the power density is governed by the amount of dielectric and/or magnetic loss within the targeted tissue. The dielectric and magnetic loss is frequency dependent and follows a Debye relation with one or more peaks of maximum loss over specific frequency band(s), with substantially less loss outside those band(s). If the goal is to increase the power density within the tissue, this behavior creates a conundrum for an electromagnetic wave source at a fixed frequency that has limits in total voltage and electric/magnetic field strength: If the operating frequency of the electromagnetic source is outside the frequency band of maximize dielectric or magnetic loss, it becomes impossible to substantially induce power density within that tissue.

A possible solution, disclosed in this invention, is to modify the electromagnetic properties of the targeted tissue. In the context of a solid tumor, this can be done by incorporating custom-tailored liquid, liquid-like, or gel-like solutions/suspensions within the tumor, with the intention to shift the frequency band where the peak of the maximum dielectric/magnetic loss occurs to the operating frequency of the electromagnetic source (which is set to the frequency where the cancer cell is most sensitive).

The method to accomplish this solution follows: 1. The electromagnetic properties of the tissue being targeted are determined. 2. A solution/suspension is concocted using sterile distilled water or other sterile liquids and concentration of additives. 3. The solution/suspension is incorporated with the targeted tissue to shift the peak of dielectric or magnetic loss to the frequency of operation.

To determine the electromagnetic properties of the tissue targeted for treatment, a sample must be taken. The sample then must undergo standard electromagnetic testing to determine the frequency-dependent dielectric permittivity, magnetic permeability, dielectric loss, and magnetic loss. Once the properties are determined, a solution or suspension must be designed to shift the peak of dielectric and/or magnetic loss to the desired operating frequency. The solution/suspension can be, but not limited to, a base of sterile distilled water with a concentration of additives such as sodium chloride, glucose, amino acids, alcohol, minerals, etc. The solution/suspension can be, but not limited to, a liquid, liquid-like, a gel, or gel-like. The solution/suspension can then be incorporated in the tissue to be targeted by a variety of methods such as, but not limited to, mixing, injection, surgery, intravenously, etc.

To apply the electromagnetic waves/fields to the targeted tissues, an apparatus that can produce electromagnetic waves must be used. An example of an apparatus can be, but not limited to, a singular planar and conformal device comprised of conductive regions separated by non-conductive regions and gaps insulated by low-dielectric constant non-conductive materials. The conductive regions of the apparatus are individually connected to a single or multiple AC/RF voltage sources or amplifiers, of which are controlled to create at least one or more voltage differentials between adjacent conductive regions. The voltage differential produces and emits evanescent waves and supports reactive fields in the volume above and below the planar surface of the apparatus. When the apparatus is placed in the vicinity of biological tissue the evanescent waves penetrate and couple into the tissue. Other examples include antennas, electrodes, capacitors, etc.

The following is a detailed explanation of the figures:

FIG. 1 is a diagram of a typical example of biological tissue 102 being treated by electromagnetic fields/waves 104. The apparatus 103 emitting electromagnetic waves is powered by the time-varying electromagnetic source 100 operating at a particular voltage "V" and frequency "f" denoted by 101. The electromagnetic fields/waves 104 penetrate the biological tissue 102 where the time-varying electric and magnetic fields induce power dissipation (i.e. power density) within the biological tissue 102.

Figure 2:
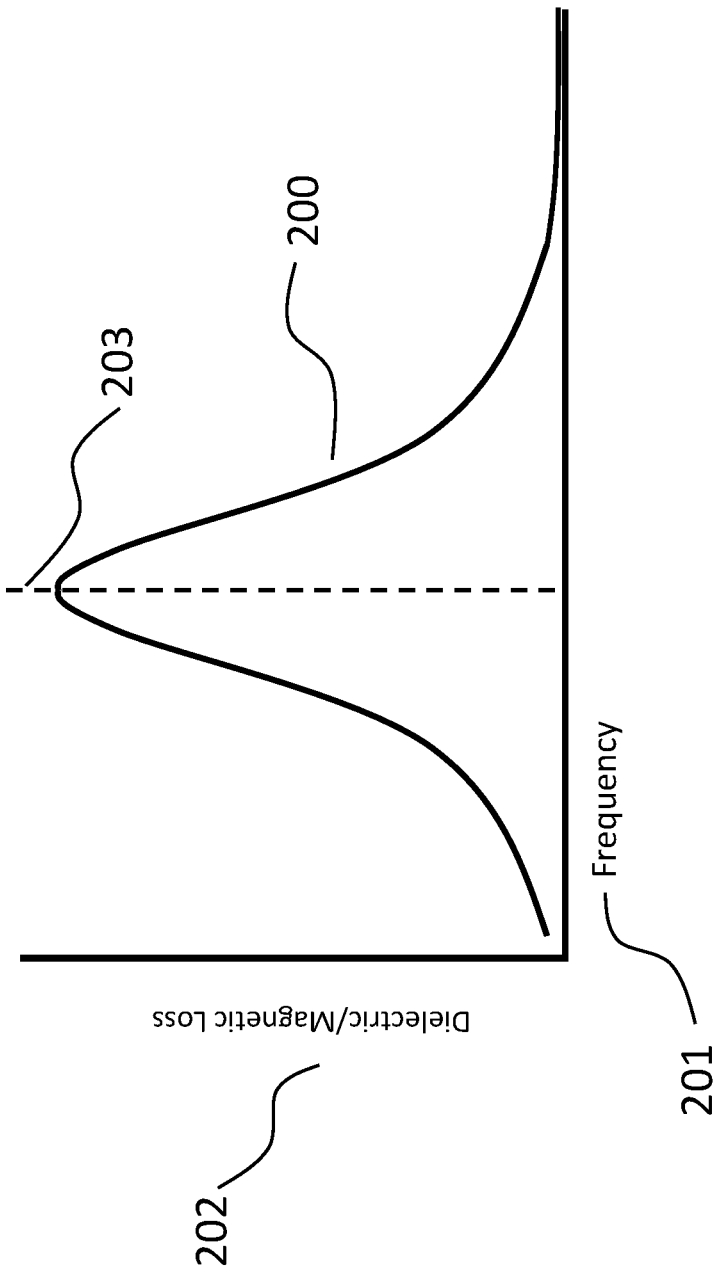
FIG. 2 shows a generalized Debye curve for dielectric or magnetic loss versus frequency of a material under illumination of an electromagnetic field.

FIG. 2 is a chart of a typical frequency-dependent dielectric and/or magnetic loss Debye relationship curve 200 of an unmodified, native material such as biological tissue. The dielectric loss 202 versus frequency 201 shows significant loss at peak frequency 203, but substantially less outside that peak frequency. If the operating frequency of the electromagnetic source is outside the band of this peak loss frequency, very little power density is induced within the targeted solution.

Figure 3:
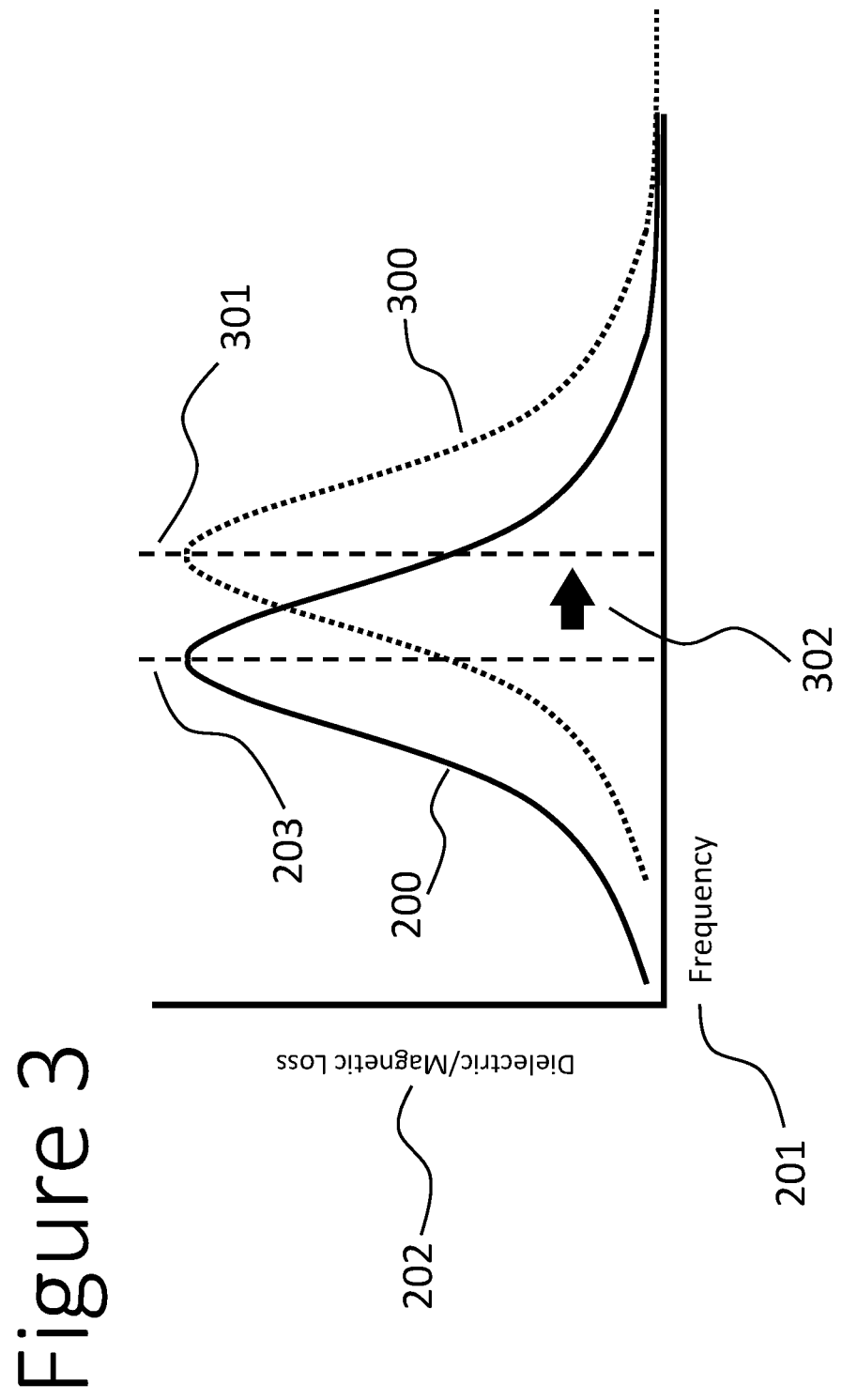
FIG. 3 shows the generalized Debye curve for dielectric or magnetic loss versus frequency of a material after being modified under the method described in this invention.

FIG. 3 is a chart of the typical frequency-dependent dielectric and/or magnetic loss Debye relationship curve 200 of an unmodified, native material along with the frequency-dependent dielectric and/or magnetic loss Debye relationship curve 300 of a modified material. As in FIG. 2, the dielectric/magnetic loss 202 is frequency dependent 201 and the unmodified material has a peak loss at a frequency 203. The modified material has a shifted peak 302 at the desired operating frequency 301. As such, the peak power density can be induced within the targeted tissue at the desired operating frequency.

Figure 4:
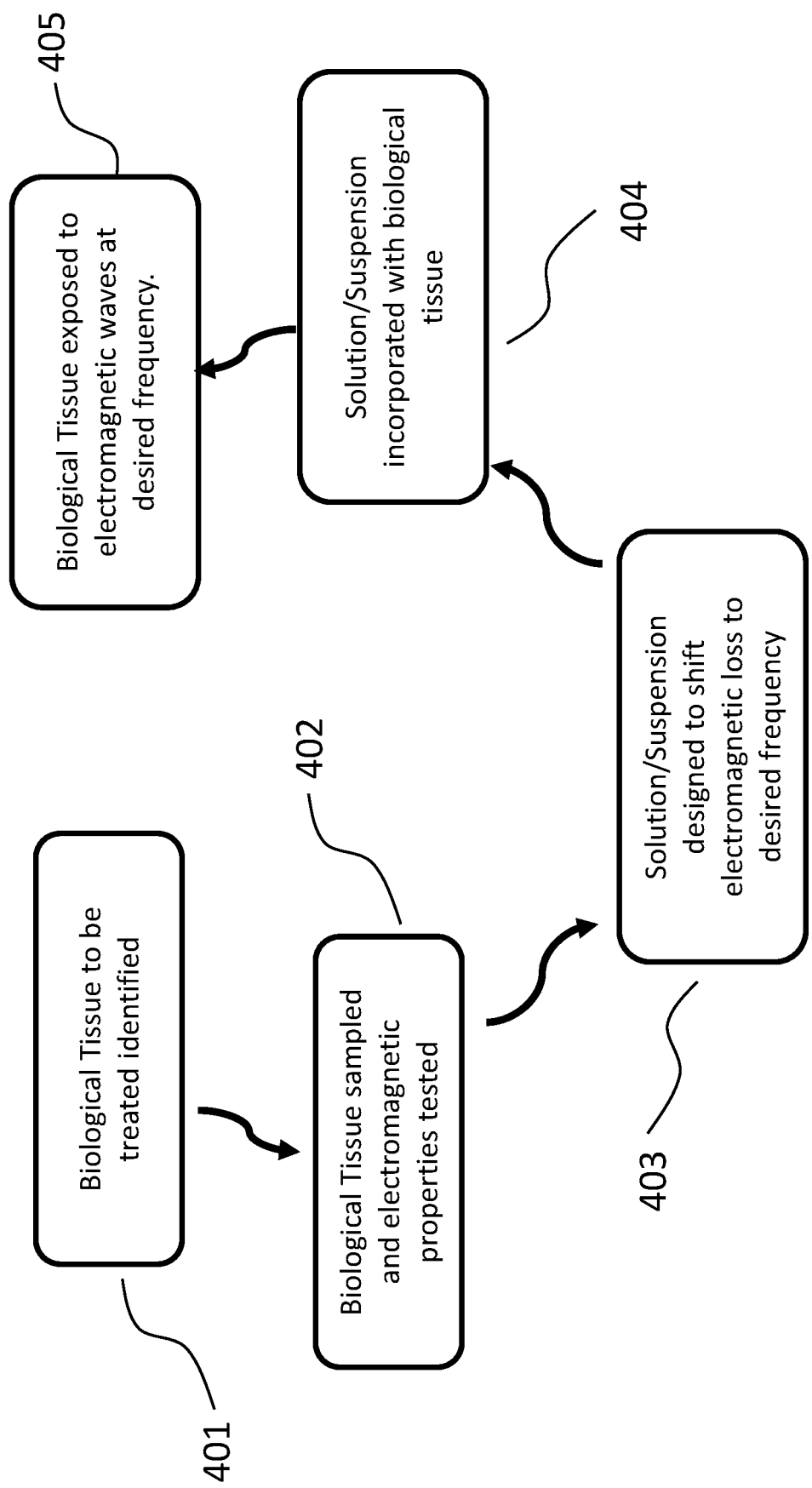
FIG. 4 is a flow chart of the method to modify the electromagnetic properties of a material for a fixed incident frequency described in this invention.

FIG. 4 is a flow-chart of the method to determine, concoct, and incorporate the modifying solution/suspension into a targeted biological tissue such as a cancer tumor. Firstly, the biological tissue that is intended to be treated must be identified as shown in box 401. Secondly, as shown in box 402, the biological tissue identified in 401 must be sampled and its electromagnetic properties must be determined. Once determined, the solution/suspension must be designed to shift the dielectric/magnetic loss peak frequency to the operating frequency of the electromagnetic source and optimum treatment 403. Next, the solution/suspension must be incorporated within the targeted tissue 404. Finally, the biological tissue must be exposed to electromagnetic waves/fields at the desired operating frequency 405.

Figure 5:
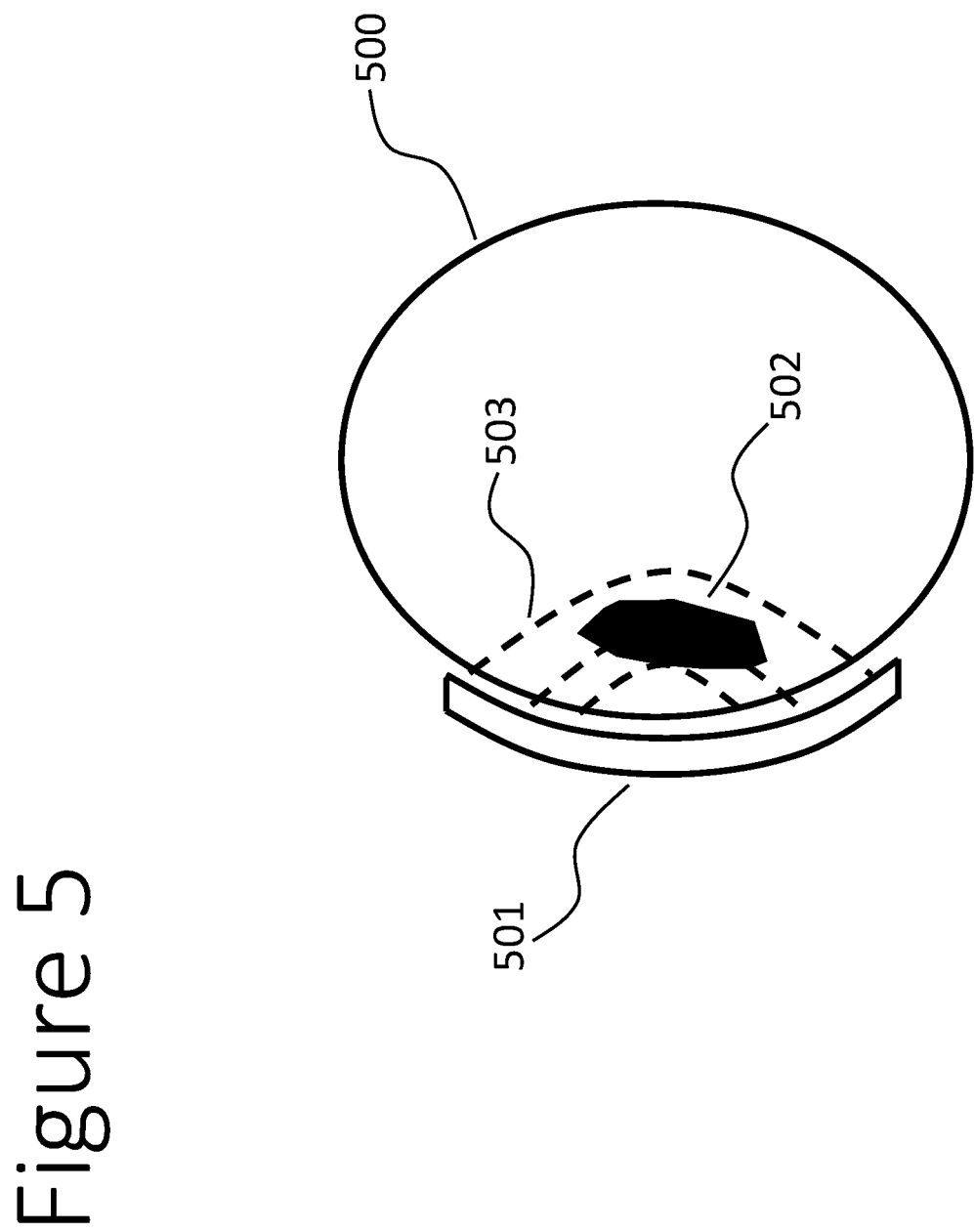
FIG. 5 is a drawing of a human brain fitted with a conformal apparatus that generates electromagnetic waves with a modified tumor under treatment.

FIG. 5 is a diagram of a conformal apparatus 501 emitting electromagnetic waves/fields 503 into the human head 500. A certain portion of the electromagnetic waves/fields 503 is penetrating a brain cancer tumor 502 where the fields/waves present within the tumor 502 induces power density (and subsequent power dissipation) that can effectively treat the tumor. This is an example of possible treatment that this method can potentially enhance.

What is claimed is:

1. A method for processing at least one frequency-dependent electromagnetic property of a solid tumor cancer to increase an absorption of an electromagnetic power characterized by a predetermined frequency range from 50 kHz to 50 MHz coupled to a target region of the solid tumor cancer, the method comprising:
   identifying the at least one frequency-dependent electromagnetic property of the target region of the solid tumor cancer;
   introducing a fluid to the target region to create a heterogenous mixture comprising the fluid and tissue from the target region of the solid tumor cancer such that the fluid is incorporated into the tissue of the target region to shift the aforementioned at least one frequency-dependent electromagnetic property to cause an increase of the absorption of electromagnetic power within the predetermined frequency range;
   supplying electromagnetic energy from a source to emit an electromagnetic field within the predetermined frequency range; and
   coupling the electromagnetic field to the target region such that one or more cells within the target region are disrupted during mitosis by an enhanced interaction of the electromagnetic field and the target region with the increased absorption of the electromagnetic power within the predetermined frequency range.

2. The method of claim 1 wherein the target region with the increased absorption is characterized by a peak of an electromagnetic loss according to a Debye relationship versus frequency; wherein the increased absorption ranges from 2 to 1000 times; wherein the one or more cells within the target region are disrupted such that the one or more cells die during mitosis.

3. The method of claim 1 wherein the predetermined frequency range is 50 kHz to 1 MHz.

4. The method of claim 1 wherein the predetermined frequency range is 50 kHz to 500 kHz.

5. The method of claim 1 wherein the fluid is a solution, suspension, a gel, or gel-like material.

6. The method of claim 1 wherein the fluid comprises a pure water combined with a concentration of additives including a sodium, a glucose, an amino acid, or a mineral.

7. The method of claim 1 wherein the method of introducing of the fluid is selected from a process including an injection, a mixing, or a surgery.

8. The method of claim 1 wherein the heterogenous mixture of the solid tumor cancer and the fluid shifts the peak of electromagnetic loss to the predetermined frequency range.

9. The method of claim 1 wherein the target region comprises a brain tumor, a breast cancer, a pancreatic cancer, a lung cancer, an ovarian cancer, or a liver cancer.

10. The method of claim 1 wherein the source is coupled to an applicator that emits the electromagnetic field, the applicator being selected from an antenna, an evanescent wave generator, a capacitor, an inductive loop, or a pair of electrodes.

11. The method of claim 1 wherein the electromagnetic field is a single fixed frequency or a plurality of frequencies and is comprised substantially of evanescent waves.

12. A method for processing at least one frequency-dependent electromagnetic property of a biological tissue to increase an absorption of an electromagnetic power characterized within a predetermined frequency range from 50 kHz to 50 MHz coupled to a target region of the biological tissue, the method comprising:
- identifying the at least one frequency-dependent electromagnetic property of the target region of the biological tissue;
- introducing a fluid to the target region to create a heterogenous mixture comprising the fluid and tissue from the target region of the biological tissue such that the fluid or incorporated into the tissue of the target region to shift the aforementioned at least one frequency-dependent electromagnetic property to cause an increase of the absorption of electromagnetic power within the predetermined frequency range;
- supplying electromagnetic energy from a source to emit an electromagnetic field within the predetermined frequency range; and
- coupling the electromagnetic field to the target region such that one or more cells within the target region are affected by an enhanced interaction of the electromagnetic field and the target region with the increased absorption of the electromagnetic power within the predetermined frequency range.

13. The method of claim 12 wherein the predetermined frequency range is 50 kHz to 500 kHz.

14. The method of claim 12 wherein the fluid is a solution, suspension, a gel, or gel-like material.

15. The method of claim 12 wherein the fluid comprises a pure water combined with a concentration of additives including a sodium, a glucose, an amino acid, or a mineral.

16. The method of claim 12 wherein the method of introducing of the fluid is selected from a process including an injection, a mixing, or a surgery.

17. The method of claim 12 wherein the heterogenous mixture of the biological tissue and the fluid shifts the peak of electromagnetic loss to the predetermined frequency range.

18. The method of claim 12 wherein the source is coupled to an applicator that emits the electromagnetic field, the applicator being selected from an antenna, a wave-launcher, a capacitor, an inductive loop, or a pair of electrodes.

19. The method of claim 12 wherein the electromagnetic field is a single fixed frequency or a plurality of frequencies.

20. A method for processing at least one frequency-dependent electromagnetic property of a solid tumor cancer to increase an absorption of an electromagnetic power characterized within a predetermined frequency range from 50 kHz to 50 MHz coupled to a target region of the solid tumor cancer, the method comprising:
- identifying the at least one frequency-dependent electromagnetic property of the target region of the solid tumor cancer;
- injecting using a syringe a fluid to the target region to create a heterogenous mixture comprising the fluid and tissue from the target region of the solid tumor cancer such that the fluid is incorporated into the tissue of the target region to shift the aforementioned at least one frequency-dependent electromagnetic property to cause an increase of the absorption of electromagnetic power within the predetermined frequency range;
- supplying electromagnetic energy from a source to emit evanescent waves within the predetermined frequency range; and
- coupling the electromagnetic field to the target region such that one or more cells within the target region are disrupted during mitosis by an enhanced interaction of the electromagnetic field and the target region with the increased absorption of the electromagnetic power within the predetermined frequency range.

* * * * *